(12) United States Patent
Petit

(10) Patent No.: US 8,142,504 B2
(45) Date of Patent: Mar. 27, 2012

(54) SYSTEM FOR FIXING A PART TO A BONE ELEMENT

(75) Inventor: Dominique Petit, Verton (FR)

(73) Assignee: Spinevision, Paris (FR)

( * ) Notice: Subject to any disclaimer, the term of this patent is extended or adjusted under 35 U.S.C. 154(b) by 1349 days.

(21) Appl. No.: 10/504,388

(22) PCT Filed: Feb. 11, 2003

(86) PCT No.: PCT/FR03/00438
§ 371 (c)(1),
(2), (4) Date: Aug. 10, 2004

(87) PCT Pub. No.: WO03/068112
PCT Pub. Date: Aug. 21, 2003

(65) Prior Publication Data
US 2005/0143733 A1    Jun. 30, 2005

(30) Foreign Application Priority Data
Feb. 11, 2002  (FR) ...................................... 02 01654

(51) Int. Cl.
*A61F 2/44* (2006.01)
(52) U.S. Cl. .................................. 623/17.11; 623/16.11
(58) Field of Classification Search .... 623/17.11–17.16; 606/246, 279; *A61F 2/44*
See application file for complete search history.

(56) References Cited

U.S. PATENT DOCUMENTS

| 4,038,703 | A | | 8/1977 | Bokros |
| 5,263,953 | A | | 11/1993 | Bagby |
| 5,423,817 | A | | 6/1995 | Lin |
| 5,662,683 | A | * | 9/1997 | Kay ............................... 606/232 |
| 6,143,032 | A | * | 11/2000 | Schafer et al. ............. 623/17.11 |
| 6,544,265 | B2 | * | 4/2003 | Lieberman ..................... 606/247 |
| 6,758,849 | B1 | * | 7/2004 | Michelson .................... 606/247 |
| 2002/0055737 | A1 | * | 5/2002 | Lieberman ....................... 606/61 |

FOREIGN PATENT DOCUMENTS

| FR | 2 812 188 A1 | 2/2002 |
| WO | WO 98/02117 | 1/1998 |
| WO | WO 98/48738 | 11/1998 |
| WO | WO 9848738 A1 * | 11/1998 |

* cited by examiner

*Primary Examiner* — Thomas J Sweet
*Assistant Examiner* — Jason-Dennis Stewart
(74) *Attorney, Agent, or Firm* — Bachman & LaPointe, P.C.

(57) ABSTRACT

The invention relates to a system which is used to fix a part to a bone element. The invention is essentially characterized in that it consists of: at least one hole which is disposed in part; a rigid rod comprising a first end, the rod being wound into a spiral along a first helicoidal curve; and a device for rotating the rod around the axis of the first helicoidal curve, such that the first end of the rod moves alternatively inside and outside the bone element and, during the rotation thereof, the first end of the rod moves at least once into the opening. The invention is particularly suitable for fixing intervertebral disks or fusion cages to the vertebral bodies of two consecutive vertebrae.

19 Claims, 2 Drawing Sheets

SYSTEM FOR FIXING A PART TO A BONE ELEMENT

BACKGROUND OF THE INVENTION (1) Field of the Invention

The present invention concerns systems for fixing a part to a bone element, with a particularly advantageous application in the spinal sector, for example for fixing an interbody cage or an intervertebral disk to the vertebral bodies of two consecutive vertebrae.

(2) Prior Art

Intervertebral prostheses which are implanted between the two vertebral bodies of two vertebrae are already known. These prostheses comprise, for example, plates which have to be fixed, respectively, to the two vertebral bodies.

When fixing a part, for example a metal part, to a bone element, and when wanting this part to be immediately integral with this bone element, screws or the like are generally used. It sometimes happens, however, that the location of this part relative to the bone element on which it is to be fixed does not permit the use of screws or the like, because there is insufficient clearance in front of the part relative to the bone element to be able to pre-position the screws before screwing them into the bone element by passing them first through slots or the like made in said part.

To remedy this problem, means such as spikes, ribs, etc., are used which are anchored in the surface part of the bone element. However, in this case the connection between the part and the bone element can only be obtained through natural growth of bone, that is to say by osteosynthesis, by interposing, if necessary, a material which promotes this osteosynthesis, for example hydroxyapatite and/or a porous or nonporous biocompatible material, or similar.

This last solution is not practical because, in this case, the patient in whom such a prosthetic part is implanted has to be told to avoid making excessive movements until definitive connection is obtained through osteosynthesis.

SUMMARY OF THE INVENTION

Therefore, it is an object of the present invention to make available a system which remedies the above-mentioned disadvantages of the systems of the prior art for fixing a part, for example a metal part, to a bone element, and with a particularly advantageous application in spinal prostheses.

More precisely, the subject of the present invention is a system for fixing a part to a bone element.

This system comprises:
a rod comprising a first end, said rod being wound into a spiral substantially along a first helicoidal curve with respect to a longitudinal axis, and
at least one through-hole made in said part and having an axial line,
means for driving said rod in rotation about the axis of said first helicoidal curve in such a way that the first end of said rod moves alternately into the element and out of said element and that, in its movement of rotation, said first end of the rod moves at least once into said through-hole.

The part to be fixed to the bone element preferably comprises a plurality of through-holes, the axial lines of these through-holes being substantially perpendicular to the longitudinal axis of the first helicoidal curve, the cross section of the holes of this said plurality of through-holes being at least equal to the maximum cross section of said rod.

The axial line or lines of the through-hole or through-holes is/are straight and substantially perpendicular to the longitudinal axis of the first helicoidal curve, or defined substantially along a second helicoidal curve.

Said part to be fixed preferably comprises a projecting rib, the height of said rib, taken from the edges of said through-holes, being less than the internal diameter of the spiral, and this rib being formed preferably along an axial line substantially parallel to the longitudinal axis of the first helicoidal curve.

The cross section of said rod can have substantially the shape of a rectangular quadrilateral, a circle, or any other shape.

Said first and second helicoidal curves are preferably substantially identical, and the first and/or second helicoidal curve or curves is or are also preferably of constant pitch.

The through-hole(s) preferably comprise(s) in each case at least one ramp bordering at least one end, respectively, of each through-hole in order to guide the movement of the first end of said rod into said holes.

In one variant, the means for driving the rod in rotation about the axis of the first helicoidal curve comprise a head integral with the second end of said rod, said head comprising means able to cooperate with an ancillary device for driving in rotation.

In this variant, the head preferably has an annular shape whose internal and external diameters are substantially equal to the internal and external diameters of said spiral.

The number of through-holes is preferably substantially equal to the number of turns of said spiral.

The end of the rod is preferably pointed or beveled.

In one variant, said spiral has a self-cutting form.

The present invention also relates to a rod for a system according to the invention, to an interbody cage comprising at least one system according to the invention, and to an artificial intervertebral disk comprising two plates, of which at least one plate, and preferably both plates, comprise(s) a system according to the invention.

Advantageously, the system according to the invention is simple and easy to produce and to implant. It does not necessitate any great damage to the bone element.

Moreover, the system according to the invention is relatively simple to remove when necessary.

BRIEF DESCRIPTION OF THE DRAWINGS

Other characteristics and advantages of the present invention will become apparent from the following description which is not in any way intended to be limiting and is given with reference to the attached drawings, in which.

It will be noted that, although the figures represent a couple of embodiments of the subject of the invention, the same reference numbers designate the same elements irrespective of the figure in which they appear and irrespective of the way in which these elements are represented. Likewise, if elements are not specifically designated in one of the figures, their designations will be easily found by referring to another figure.

DETAILED DESCRIPTION OF THE PREFERRED EMBODIMENT(S)

Figure 1:
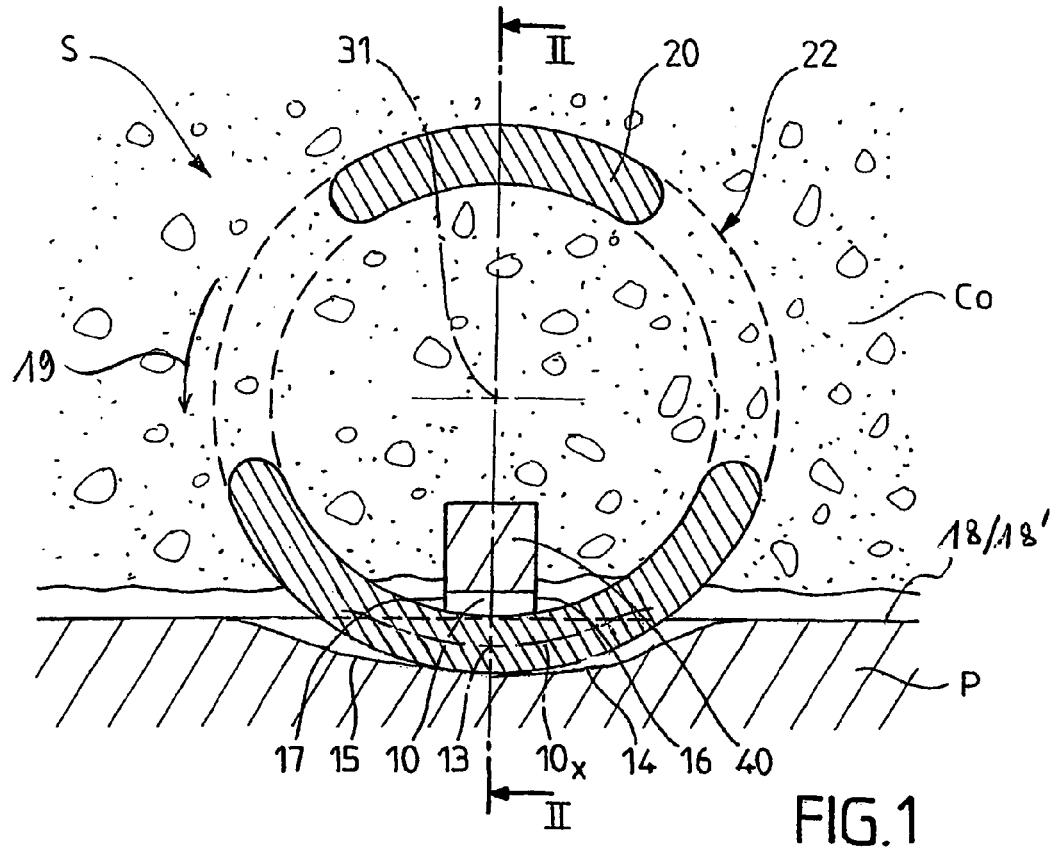
FIGS. 1 and 2 show two cross-sectional views of an embodiment of the system according to the invention for fixing a part to a bone element, FIG. 1 being a cross section designated I-I in FIG. 2, and FIG. 2 being a cross section designated II-II in FIG. 1, and FIGS. 3 and 4 represent a cross-sectional view and a cavalier projection, respectively, of another embodiment of the system according to the invention in an application for fixing two plates of an intervertebral disk to the two vertebral bodies of two consecutive vertebrae.

The present invention concerns system S for fixing a part P to a bone element Co.

The part P comprises at least one through-hole 10 formed, for example, on an outer surface 18, 18', this through-hole having an axial line 10x.

The system S is a rigid rod 20 comprising a first end 21 configured to penetrate into the element Co, the rod being wound into a spiral 22 substantially along a first helicoidal curve.

The system additionally comprises means 30 for driving the rod 20 in rotation about the axis 31 of the first helicoidal curve in such a way that the first end 21 of the rod 20 moves alternately into the element Co and out of the element, and that, in its movement of rotation outside the element Co, the first end 21 of the rod 20, which for example is pointed or beveled, moves at least once into the through-hole 10.

It will be noted that the cross section of the through-hole 10 can be circular and have a cross section slightly greater than the maximum cross section of the rod 20. In this case, the rod 20 moves only once into this hole. However, it is also possible to form a hole with an oblong cross section and a width at least equal to the maximum cross section of the rod 20 and with a length at least equal to a multiple of the pitch of the helicoidal spiral 22. In this case, the first end 21 of the rod moves, or can move, several times into the same through-hole.

This latter design is possible, but it is advantageous if the system comprises a plurality of through-holes 10, 11, 12, etc., as is illustrated in all the figures, these being formed in the part P and each having an axial line 10x, 11x, 12x, etc., respectively.

In one variant, the axial lines 10x, 11x, 12x, etc., of these through-holes are substantially defined along a second helicoidal curve, the cross section of the holes of this plurality being at least equal to the maximum cross section of the rod 20 in such a way that the rod can slide relatively easily therein.

In another variant, the through-holes 10, 11, 12, etc., are formed in the part P in such a way that their axial lines 10x, 11x, 12x, etc., are all substantially perpendicular to the same straight line 13, which is itself parallel to the axis 31, in order to promote penetration of the rod 20 into the bone and help it move more easily into these holes.

To make it easier to place the part P on the element Co and give it a relatively stable first position immediately upon fitting, it is advantageous if the system additionally comprises, as is illustrated in the figures, a projecting rib 40 formed on the part P and able to cooperate, for example by plug-type engagement, with a complementary groove formed beforehand in the bone element Co. The height of the rib, taken from the edges of the through-holes, is of course less than the internal diameter of the spiral 22.

In addition, it is highly preferable if the rib 40 is formed along an axial line substantially parallel to the axis 31 and is substantially contained within a plane defined by the straight line 13 and the axis 31 of the second helicoidal curve in spiral form 22.

This rib 40 makes it possible to improve the hold in terms of the cooperation between the walls of the through-holes and the spiral 22.

In a preferred embodiment which facilitates formation of the spiral 22, the cross section of the rod 20 has substantially the shape of a rectangular quadrilateral, for example a square or a rectangle, if appropriate a trapezoid whose large base is little different than the small one and whose shape may then be similar to that of a rectangle.

It will also be noted that the first and second helicoidal curves defined above are advantageously substantially identical and preferably have a constant pitch.

With a view to helping to guide the first end 21 of the rod 20 when it penetrates into each through-hole, the through-hole or through-holes 10, 11, 12, etc., comprise(s) in each case at least one ramp 14, 15 bordering at least one end 16, 17, respectively, of each through-hole in order to guide the movement of the first end 21 of said rod 20 into said holes. In this configuration, the axial lines 10x, 11x, 12x, etc., while remaining perpendicular to the straight line 13, are rounded transversely on a radius of curvature greater than the outer radius of the spiral 22, as can be seen from FIG. 1.

The system advantageously comprises ramps 14, 15 which border, respectively, each of the two ends 16, 17 of each through-hole.

Figure 2:
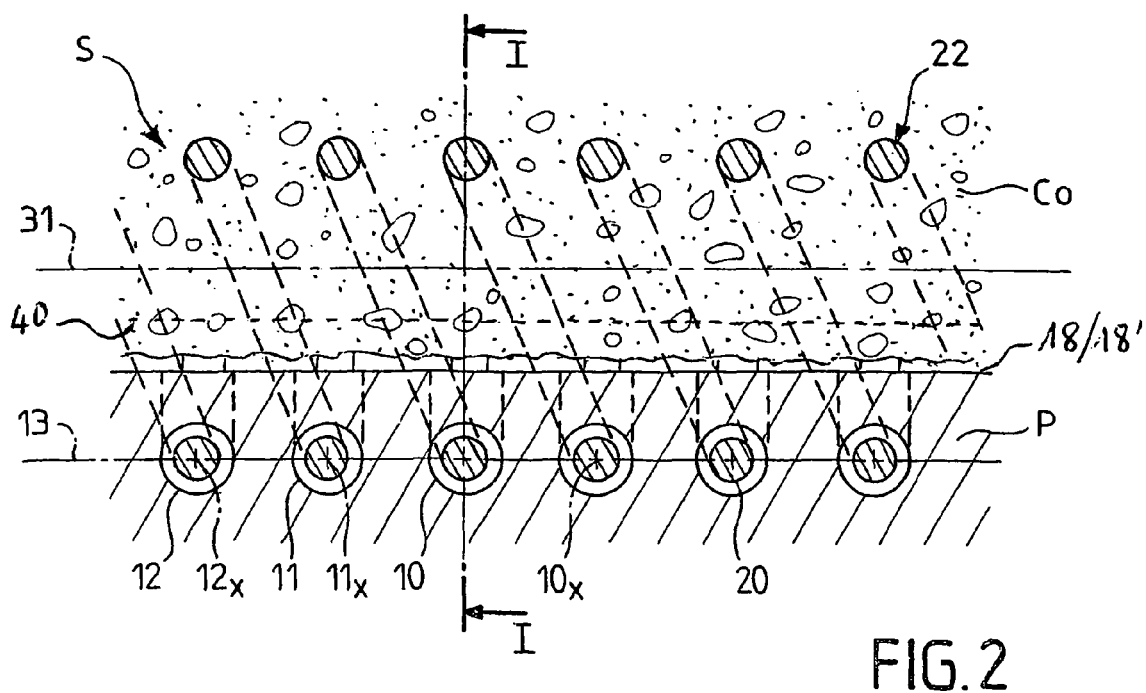
Figure 4:
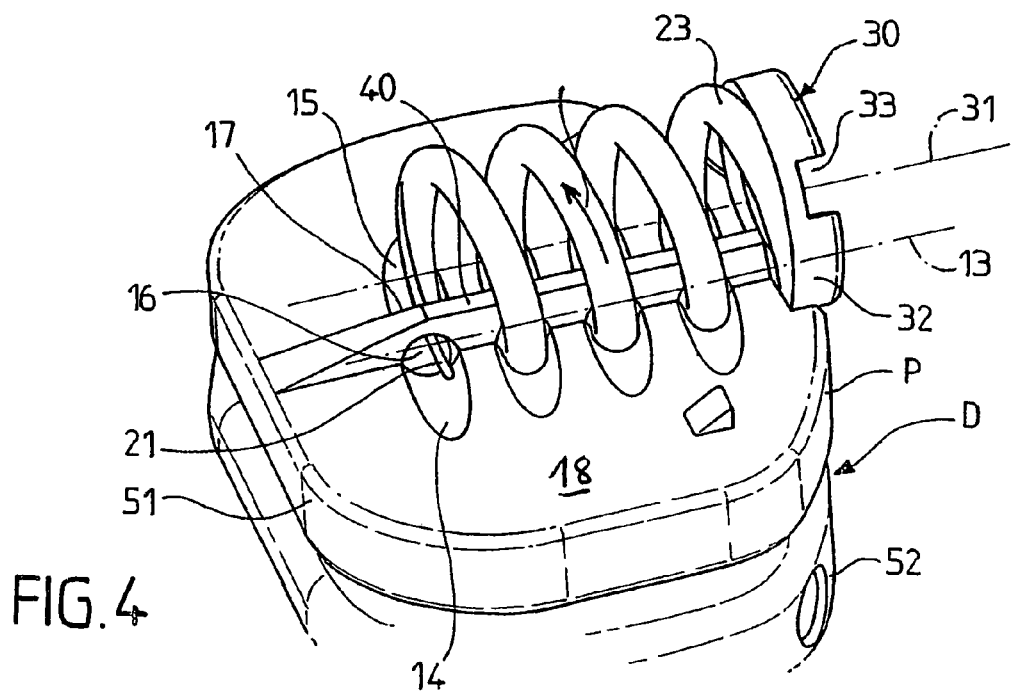

These ramps, which can be seen in FIGS. 2 and 4, adopt the shape of portions of a hollowed helicoidal surface very close to that of the outer surface of the spiral 22 defined above.

As was mentioned above, the system comprises means 30 for driving the rod 20 in rotation about the axis 31 of the second helicoidal curve. These means can, for example, consist of the second end 23 of the rod 20 in spiral form 22. However, it is preferable if they comprise a head 32 integral with this second end 23 of the rod 20, this head comprising means 33 for cooperating with an ancillary device for driving in rotation, for example equivalent to a screwdriver, a tubular wrench, or similar.

It is also very advantageous if the head 32 has an annular shape whose internal and external diameters are substantially equal to the internal and external diameters of the spiral 22, it thus being possible to simultaneously form the spiral 22 and the head 32, by machining of a cylindrical tube made of titanium or the like.

Figure 3:
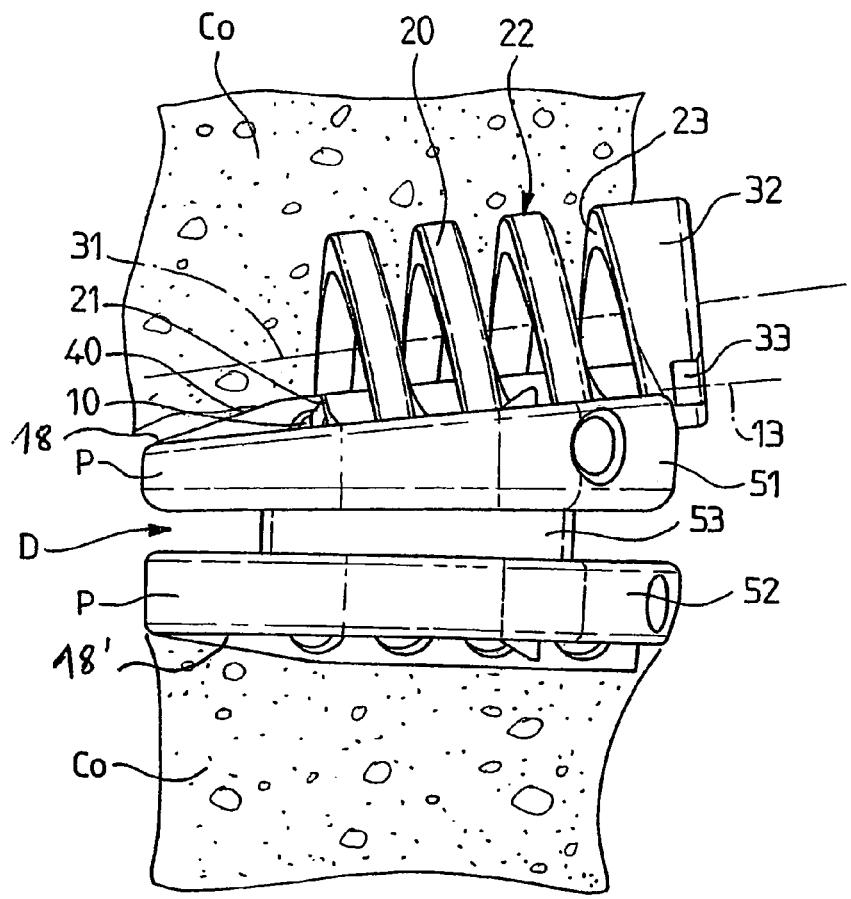

This embodiment of the head in an annular shape also affords an advantage when fitting the spiral in place. This is because the head then serves as an abutment for defining the limit position of the spiral 22 relative to the part P, as is illustrated in FIGS. 3 and 4.

In a preferred possible embodiment, the number of holes 10, 11, 12, etc., is substantially equal to the number of turns of the spiral 22, by which means it is possible to obtain relatively good fixation of the part P on the bone element Co, with a minimum length of the spiral.

The system according to the invention can be used in numerous fields, but it is particularly advantageous for procedures for fixing interbody cages or intervertebral disks.

To make implantation of the system according to the invention easier, it may be necessary first of all to cut a thread in the bone element in order to form, in the wall, a substantially helicoidal shape which exactly complements the shape of the spiral 22. This operation is then performed with the aid of a thread-cutting instrument.

Once the thread has been cut, the spiral of the prosthesis is screwed into the thread.

It is also possible to use a self-cutting spiral. This eliminates the step of first cutting a thread in the bone element. The spiral 22 of the prosthesis is in this case screwed directly into the bone element.

FIGS. 3 and 4 show, by way of example, the system according to the invention used for fixing the two plates 51, 52 of an artificial intervertebral disk D, cooperating with one another by hinge means 53 or similar, respectively to the two vertebral bodies of two consecutive vertebrae.

In this case, the system as described above functions and is employed in the following way:

When, for example, it is necessary to implant an artificial intervertebral disk D between two vertebral bodies, it is introduced by sliding it between the two vertebral bodies, which if necessary have first been subjected to a slight distraction. Two helicoidal rods in spiral form 22 are then introduced, as has been described above, by moving alternately into the bone of the vertebral bodies and respectively into the through-holes of each plate of the intervertebral disk, the first end 21 of each rod moving into a hole 10, 11, 12, etc., upon each complete turn of the spiral when the rod is driven in rotation by the head 32.

In FIGS. 1 and 4, the arrow 19 illustrates the direction in which the spiral 22 is screwed into the vertebral structure for implantation of the system S.

The system according to the invention will be used, in the same way as described above, for fixing at least one of the two opposite outer surfaces of an interbody cage to at least one of the two vertebral bodies of two consecutive vertebrae, the through-holes being formed on the opposite faces of the cage.

The fixation system described above has two important advantages compared to those systems of the prior art which only comprised spikes and/or ribs, if appropriate with products promoting osteosynthesis between the opposing faces coming into contact, respectively, with the plates and the vertebral bodies.

The first of these two advantages is the fact that it is therefore possible to introduce the intervertebral disk or the cage without having to ensure considerable distraction between the two vertebral bodies, whereas, with the systems of the prior art, it was necessary for the two vertebral bodies to undergo distraction by at least a value twice the height of the spikes and/or ribs.

The second of these two advantages is the fact that the fixation makes it possible to obtain what technicians call primary stability, which allows the patient to make movements not permissible with the systems of the prior art which required waiting for extensive consolidation of the bone to take place, generally a period of the order of several weeks.

To remove the system S, the spiral is simply unscrewed by turning the cage in the direction opposite to the arrow 19. It is not necessary to break the bone element in order to free the spiral 22.

The invention is described above by way of example. It goes without saying that the skilled person will be able to form different variants of the invention without thereby departing from the scope of the patent.

The invention claimed is:

1. A system comprising:
   a rod comprising a first end, said rod being wound into a spiral substantially along a first helicoidal curve with respect to a longitudinal axis,
   a part configured to be inserted between two adjacent vertebrae, said part having at least one pre-formed through-hole in an outer surface adapted to be in contact with a face of one of said two adjacent vertebrae, said pre-formed through-hole having an axial line,
   means for rotatably driving said rod about the longitudinal axis so that upon rotatably driving the rod, the first end of said rod can move alternately into a bone and out of said bone and for driving said rod outside of the bone so that said first end of the rod moves at least once into said at least one pre-formed through-hole in said part, and the axial line of said at least one pre-formed through-hole being perpendicular to a longitudinal axis of said rod when said rod moves into the at least one pre-formed through-hole.

2. The system as claimed in claim 1, wherein said part has a plurality of pre-formed through-holes, the axial lines of said pre-formed through-holes being substantially perpendicular to the longitudinal axis, and a cross section of the holes of said plurality of pre-formed through-holes being at least equal to a maximum cross section of said rod.

3. The system as claimed in claim 1, wherein the axial line of each said pre-formed through-hole is straight and substantially perpendicular to the longitudinal axis.

4. The system as claimed in claim 1, wherein the axial line of each said pre-formed through-hole is defined substantially along a second helicoidal curve.

5. The system as claimed in claim 4, wherein said first and second helicoidal curves are substantially identical.

6. The system as claimed in claim 4, wherein at least one of the first and second helicoidal curves is of constant pitch.

7. The system as claimed in claim 1, wherein a cross section of said rod has substantially a rectangular quadrilateral shape.

8. The system as claimed in claim 1, wherein a cross section of said rod has a substantially circular shape.

9. The system as claimed in claim 1, wherein the at least one pre-formed through-hole comprises in each case at least one ramp bordering at least one end, respectively, of each said pre-formed through-hole in order to guide the movement of the first end of said rod into said at least one pre-formed through-hole.

10. The system as claimed in claim 1, wherein the means for driving the rod in rotation about the longitudinal axis of the first helicoidal curve comprise a head integral with a second end of said rod, said head comprising means for cooperating with an ancillary device for driving in rotation.

11. The system as claimed in claim 10, wherein the head has an annular shape whose internal and external diameters are substantially equal to the internal and external diameters of said spiral.

12. The system as claimed in claim 1, wherein the first end of the rod is pointed or beveled.

13. The system as claimed in claim 1, wherein the number of said pre-formed through-holes is substantially equal to the number of turns of said spiral.

14. The system as claimed in claim 1, wherein said spiral has a self-cutting form.

15. An interbody cage comprising at least one system as claimed in claim 1, wherein said cage comprises said part having at least one pre-formed through-hole.

16. An interbody cage according to claim 15, wherein said cage has a plurality of pre-formed through-holes.

17. A system according to claim 1, wherein said first end of said rod is threaded through a bone and said at least one pre-formed through hole in said part by said rotatable driving means so as to join said part to said bone.

18. A system comprising:
   a rod comprising a first end, said rod being wound into a spiral substantially along a first helicoidal curve with respect to a longitudinal axis,
   a part adapted to be inserted between two adjacent vertebrae, said part having at least one pre-formed through-hole made in an outer surface adapted to be in contact with a face of one of the two adjacent vertebrae, said pre-formed through-hole having an axial line,
   means for rotatably driving said rod about the longitudinal axis so that upon rotatably driving the rod, the first end of said rod can move alternately into a bone and out of said bone and that, in its movement of rotation, said first end of the rod moves at least once into said pre-formed through-hole, said part having a plurality of pre-formed through-holes, the axial lines of said pre-formed through-holes being substantially perpendicular to the longitudinal axis and being parallel to each other, and a cross section of the holes of said plurality of pre-formed through-holes being at least equal to a maximum cross section of said rod, and said part having a projecting rib with a height taken from the edges of said pre-formed through-holes being less than an internal diameter of the spiral.

19. The system as claimed in claim 18, wherein said rib is formed along an axial line substantially parallel to the longitudinal axis.

* * * * *